US012156841B2

(12) United States Patent
Ahmed

(10) Patent No.: US 12,156,841 B2
(45) Date of Patent: Dec. 3, 2024

(54) EXOSKELETON ROBOT FOR MOTOR REHABILITATION OF THE HAND AND WRIST

(71) Applicant: Bahy Ahmed Mohamed Kamel Ahmed, Cairo (EG)

(72) Inventor: Bahy Ahmed Mohamed Kamel Ahmed, Cairo (EG)

( * ) Notice: Subject to any disclaimer, the term of this patent is extended or adjusted under 35 U.S.C. 154(b) by 697 days.

(21) Appl. No.: 17/423,807

(22) PCT Filed: Jan. 16, 2020

(86) PCT No.: PCT/EG2020/000003
§ 371 (c)(1),
(2) Date: Jul. 16, 2021

(87) PCT Pub. No.: WO2020/147913
PCT Pub. Date: Jul. 23, 2020

(65) Prior Publication Data
US 2022/0079831 A1   Mar. 17, 2022

(30) Foreign Application Priority Data
Jan. 16, 2019 (EG) .............................. 2019010080

(51) Int. Cl.
*A61H 1/02* (2006.01)
*A61H 23/02* (2006.01)
(Continued)

(52) U.S. Cl.
CPC ........... *A61H 1/0288* (2013.01); *A61H 23/02* (2013.01); *B25J 9/1633* (2013.01); *G16H 20/30* (2018.01);
(Continued)

(58) Field of Classification Search
CPC ...... A61H 1/0285; A61H 1/0288; A61H 1/00; B25J 9/0006; B25J 9/1633
See application file for complete search history.

(56) References Cited

U.S. PATENT DOCUMENTS 4,986,280 A * 1/1991 Marcus .................... B25J 19/02
600/595
6,110,130 A * 8/2000 Kramer .................. B25J 9/0006
600/595
(Continued)

FOREIGN PATENT DOCUMENTS

CN      101433491 A    5/2009
CN      201394837 Y    2/2010
(Continued)

*Primary Examiner* — Joseph D. Boecker
*Assistant Examiner* — Thomas W Greig
(74) *Attorney, Agent, or Firm* — Accelerate IP LLC

(57) ABSTRACT

An exoskeleton robot for hand and wrist kinetic rehabilitation provides passive, active-assisted, and active resistance rehabilitation for fingers and wrist joints independently. It relieves pain during exercises and stimulates the mechanoreceptors for all hand and wrist joints. The device provides levels of differentiation for finger rehabilitation through independent motion control mechanisms for all ten phalanges of the fingers and the wrist with a full range of motion, which helps in focusing the work on each joint selectively. It is portable, operates using an electric power source only, easy to wear, fits different hand sizes, and most of its parts made of lightweight plastic.

14 Claims, 12 Drawing Sheets

(51) Int. Cl.
    *B25J 9/16*         (2006.01)
    *G16H 20/30*     (2018.01)

(52) U.S. Cl.
    CPC .......... *A61H 2201/1215* (2013.01); *A61H 2201/149* (2013.01); *A61H 2201/1638* (2013.01); *A61H 2201/1647* (2013.01); *A61H 2201/165* (2013.01); *A61H 2201/5012* (2013.01); *A61H 2201/5043* (2013.01); *A61H 2201/5061* (2013.01); *A61H 2201/5064* (2013.01); *A61H 2201/5097* (2013.01)

(56) References Cited

U.S. PATENT DOCUMENTS

| | | | |
|---|---|---|---|
| 6,827,579 | B2 | 12/2004 | Burdea et al. |
| 2010/0305717 | A1* | 12/2010 | Tong ............ A63B 21/4019 623/64 |
| 2014/0288664 | A1* | 9/2014 | Miyazawa ............ A61F 2/586 623/24 |
| 2016/0259417 | A1* | 9/2016 | Gu .................... G06F 3/014 |
| 2017/0266075 | A1* | 9/2017 | Becchi .................. A63B 23/16 |
| 2020/0121478 | A1* | 4/2020 | Woge .................. B25J 9/0006 |

FOREIGN PATENT DOCUMENTS

| | | |
|---|---|---|
| CN | 105726263 A | 7/2016 |
| CN | 105796283 A | 7/2016 |
| CN | 106264983 A | 1/2017 |
| CN | 106994086 A | 8/2017 |
| CN | 107212996 A | 9/2017 |
| CN | 109199784 A | 1/2019 |
| CN | 107212996 B | 3/2019 |
| CN | 209630102 U | 11/2019 |
| MX | 2015001947 A1 * | 8/2016 |
| WO | WO-2018/036571 A1 | 3/2018 |

* cited by examiner

EXOSKELETON ROBOT FOR MOTOR REHABILITATION OF THE HAND AND WRIST

CROSS-REFERENCE TO RELATED APPLICATIONS

This application is a national stage entry of International Patent Application No. PCT/EG2020/000003, filed on Jan. 16, 2020, which claims priority to and the benefit of Egypt Application No. 201901080, filed on Jan. 16, 2019, the entire contents of all of which are incorporated herein by reference in their entirety.

FIELD OF THE INVENTION

This invention relates, generally, to rehabilitation devices. More specifically, it relates to hand and wrist motor rehabilitation exoskeletons.

BACKGROUND OF THE INVENTION

Physiotherapists and patients need rehabilitation devices in the physiotherapy sessions. So, the researchers began to research practical experiments that have demonstrated the positive effects of using rehabilitation devices in motor rehabilitation. Currently, various systems help in the rehabilitation process of the upper limbs ranging from the shoulder to the fingers of the patient's hand. Some of these systems are already registered and offered for sale, then some of them are mentioned:
1—(U.S. Pat. No. 4,986,280, Jan. 22, 1991) describes a system for measuring the relative angular direction of two skeletal movable hand joints, which are proportionally joined at a hinge.
2—James F. Kramer filed U.S. Pat. No. 6,110,130 on Aug. 29, 2000, for an exoskeleton of the hand that provides the measurement of the position and angles of the phalanges of the fingers for application in areas such as virtual reality, remote robotics, animation and medical assessment of hand function.
3—The European Patent Office has filed an invention with the patent number "CN 101433491", offering the robot as a garment to restore hand function through rehabilitation procedures.
4—"Method and Device for the Rehabilitation of Neurological Movement Disorders" "U.S. Pat. No. 6,827,579 B2" and dated Dec. 7, 2004.
5—patent No. "US 2010/0305717 A1", a wearable strength assist device to help the user move their hands, provides a movement rehabilitation system for training by the user.
6—The invention "Finger Movement Functional Rehabilitation Robot" with Patent No. "CN201394837 (Y)" from EPO.
7—The invention provides a "Wearable Hand Exoskeleton Rehabilitation training robot" with the patent number "CN 105726263A".
8—The invention provides a "rehabilitation training device" with the patent number "CN 105796283 A".
9—The invention provides a "wearable rehabilitation training exoskeleton" with the patent number "CN 106264983 A".
10—The invention provides a "five finger displacement finger rehabilitation training system" with patent number "CN 106994086 A".
11—US patent No. "US 2017/0266075 A1" describes the invention as "a mobility aid and/or finger rehabilitation device or more".
12—The invention "Apparatus and Method for Active or Passive Wrist Integrated Rehabilitation Training with Fingers" with the patent number "CN107212996".
13—The invention provides "robotic orthotic devices for hand and wrist rehabilitation" with the patent number "WO 2018/036571 A1".
14—The invention provides a "flexible device for rehabilitation of the driving hand and feedback control circuit" with the patent number "CN 109199784 A".

The problem in the previous art, which we solved, is that the devices lack differentiation between the different levels of hand rehabilitation, they lack focusing and working on the joints of the hand selectively, cannot relieve pain on patients during training and stimulate the mechanoreceptors of the joints of the hand. These devices support a small number of independent degrees of freedom, most of which do not cover the patient's needs. These devices focus on training the patient to extend and flex the finger as a single block, which causes a problem for physiotherapists in transferring the patient's full motor skills. Also in many of these devices, the control of the active rehabilitation process depends on sensing the brain signals through the muscles, which causes inability to control the separate movements of the phalanges due to the strong similarity between motor signals and the many factors affecting them. The sensors are attached to the skin, making them unstable due to moisturization of the skin. Therefore, also there is the issue of non-availability of devices to assist in the rehabilitation of wrist and all the hand phalanges with high accuracy, also the device provides effective rehabilitation by extension and flexion.

SUMMARY OF THE INVENTION

An exoskeleton robot for the motor rehabilitation of the hand and wrist, comprising: ten mechanisms to control the movement of each phalange of the finger independently to form five mechanical fingers to work on the joints selectively; a mechanism to control the movement of the wrist; Four degrees of freedom for each finger (pinky, ring, middle, index and thumb), a degree of freedom for the wrist and a degree of freedom for the forearm when the device is fixed on the base; ten DC motors to generate rotational motion of the phalanges; Ten phalanx movement mechanisms consisting of the worm and the worm gear mechanism to transfer the rotational motion of the motor to a rotational motion in an axis perpendicular to the motor axis and to make the motor the sole controller of the movement with the self-locking feature; a linear motion mechanism to adjust the device to the appropriate size for the user to fit different hand sizes; an adduction and abduction movement mechanism to allows rotational motion to the right and left for each finger separately; force sensors on each phalanx of the finger to measure the force applied by the patient on all phalanges in the extension and flexion of the fingers for active-assisted and resistant rehabilitation at their different levels for each joint separately; passive, active-assisted and active resistance rehabilitation mechanisms for the wrist; a group of vibration devices on all phalanges controlled to relieve pain on patients during training and stimulate mechanoreceptors for all joints of the hand and wrist.

Our system is characterized by: the ability to control the movement of ten joints of the fingers of the hand with a full range of motion independently, which allows the device to be used in various injuries of the hand at different levels, whether it's a problem in the entire movement of the hand or a problem in a particular joint or a different level of injury to a different finger in the hand; the therapist can choose the joint and work on it with the level of training it needs, whether passive or active training, with a precise system and easy to use; the active and passive control of wrist movement with high accuracy; the active rehabilitation exercises reliance on a more stable and accurate source for measuring the force and making it the main element for controlling the level of training and movement; the vibration devices relieve pain for patients during training and stimulate mechanoreceptors for the joints of the hand; all hand rehabilitation procedures and exercises performed by the physiotherapist can be performed by the device with very high accuracy because it provides all degrees of training until the recovery of hand strength represented in passive rehabilitation, active-assisted, free active and active resistance rehabilitation; The device is worn automatically; it is portable; fits different hand sizes; lightweight.

DETAILED DESCRIPTION OF INVENTION

We present a new innovative comprehensive mechatronics design of an exoskeleton robot for kinetic rehabilitation of the hand and wrist, which is placed on the patient's hand to provide the patient's movements independently. The system consists of five mechanical fingers (thumb, index, middle, ring, and pinky finger) where each of their movements (extension and flexion) are controlled by an electronic system designed to move the exoskeleton robot for the hand with many movements in different ways to serve rehabilitation.

Figure 1:
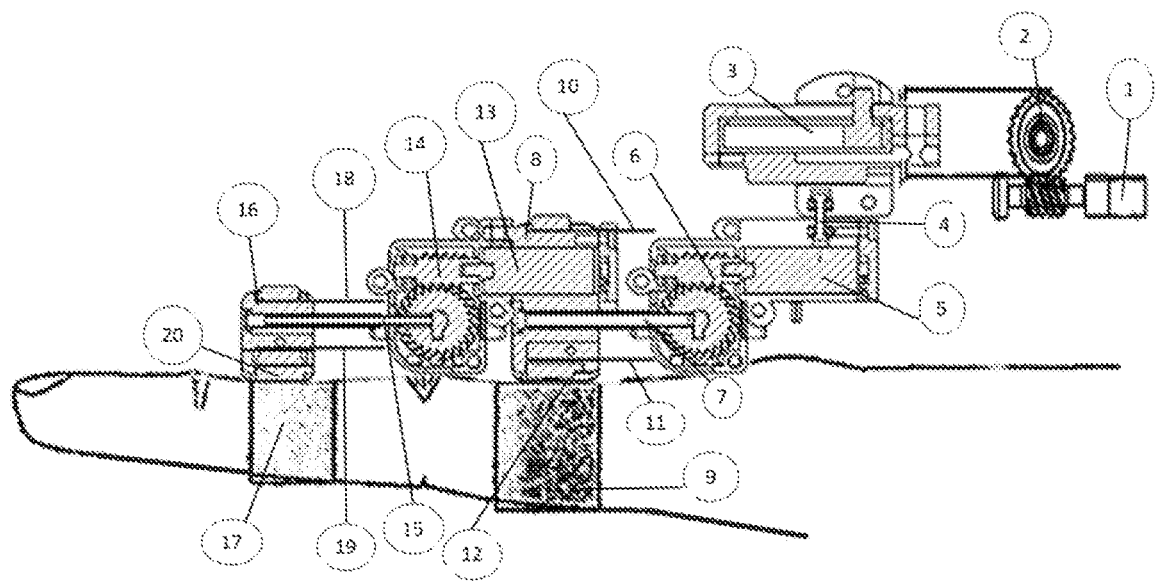
FIGS. 1 and 2 represent side views of the mechanism that was used for all fingers
  No. (1) in FIG. 1 represents the DC micro motor for wrist movement
  No. (2) in FIG. 1 represents the worm and the worm gear mechanism
  No. (3) in FIG. 1 represents the linear motion mechanism
  No. (4) in FIG. 1 represents the abduction and adduction motion mechanism
  No. (14, 6) in FIG. 1 represents a rotational motion mechanism of the proximal and middle or distal phalanges
  No. (7, 15) in FIG. 1 represents linear motion mechanism to allow the phalanges to rotate
  No. (9) in FIG. 1 represents the force sensor
  No. (13, 5) in FIG. 1 represents DC motors
  No. (8, 16) in FIG. 1 represents the solid parts that fix the phalanges
  No. (10, 11, 18, 19) in FIG. 1 represents force sensors
  No. (12, 20) in FIG. 1 represents micro-vibration motors
  No. (9, 17) in FIG. 1 represents the soft non-stretchable strap
Figure 2:
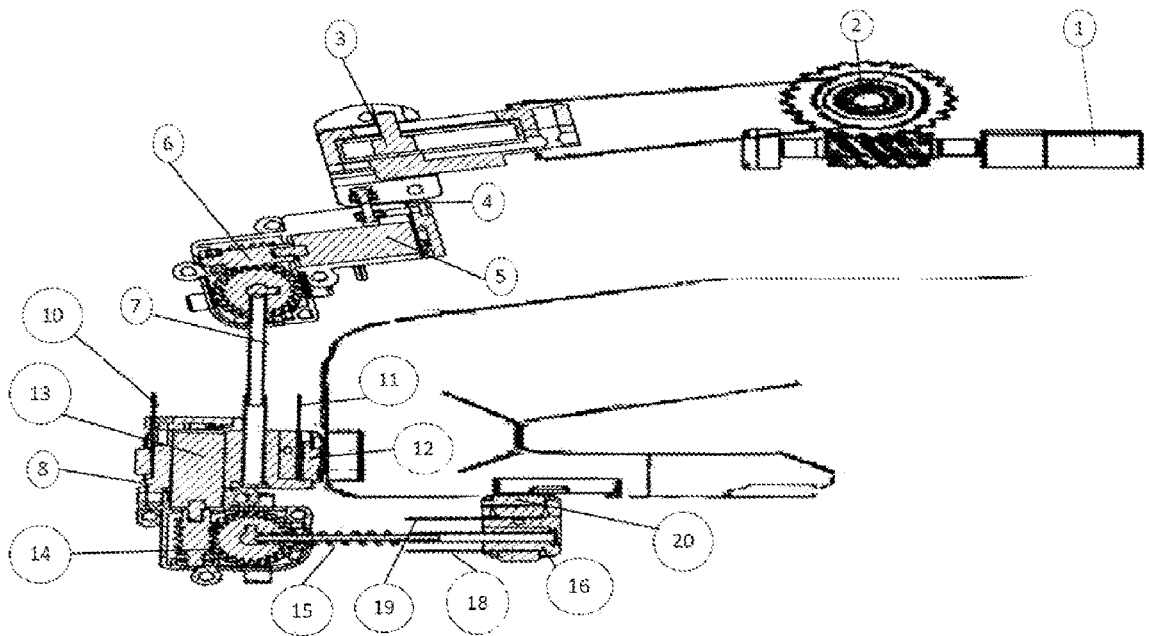

The mechanical system contains 22 degrees of freedom represented by 4 degrees of freedom for each finger of the hand (pinky, ring, middle, index, and thumb), a degree of freedom for the wrist and a degree of freedom for the forearm in the case of fixing the other parts of the device. For all fingers, the first degree of freedom relates to the linear movement, the second degree of freedom is a rotational movement representing abduction or adduction, the third degree of freedom is a rotational movement of the proximal phalanges and the fourth degree of freedom is a rotational movement of the middle or distal phalanges representing the flexion and extension movement of all the fingers of the hand. FIGS. 1 and 2 show the mechanical design of the finger force transmission system.

The electronic system consists of a control circuit that is represented in an appropriate reprogrammable microcontroller, integrated circuits (IC L9110) to operate DC motors in two directions at different speeds, force sensor readings receiving circuits, a transistor array (ULN 2803) to drive the vibration motors operation and a unit Communication for wireless transmission of information and commands from the computer to the microcontroller and vice versa.

FIGS. 1 and 2 show the lateral view of the mechanism (in the positions of extension, and flexion) that was used for all fingers consisting of the following mechanisms: the first motion is the linear displacement (3); the second motion is the abduction and adduction motion (not actuated) (4); the third and fourth motions are a rotational motion of the proximal and middle phalanges of the (index, middle and ring finger) and the proximal and distal phalanges of the little finger and thumb representing the motion of extension and flexion of the fingers (6, 14). The fifth and sixth motions are linear displacement motions to allow the phalanges to rotate and transmit force from the gearbox and allows the size to be changed to suit different hand sizes (7, 15). The seventh motion (2) is a rotational movement of the wrist. Parts (13, 5, and 1) represent the source of the kinetic energy of the design which is a micro geared DC Motor. Parts (10, 11, 18, and 19) are force sensors to provide effective rehabilitation in extension and flexion for all phalanges. Parts (12, 20) are micro-vibration motors to relieve the patent's pain on the phalanges during practice. Parts (9, 17) are soft, non-stretchable straps to fix the design on the hand with a circular piece attached to it. It is placed on the force sensor to transmit the force applied by the finger in the flexed position. Part (8) represents pieces that are fixed on the proximal phalanges to move them, inside which the motor (13) is placed in a circular shape, the force sensor (10) is placed on its surface and the belt (9) passes through it. The vibration motor (12) is placed underneath which controls the readings of the force sensor (11) that is fixed in the middle of it. Part (16) consists of pieces are fixed on the medial phalanges to move them and they are placed in a circular shape on their surface, the force sensor (18) and the strap (17) passes through it and the vibration motor (20) is placed underneath to control the readings of the force sensor (19) which is fixed in the middle of it.

Figure 3:
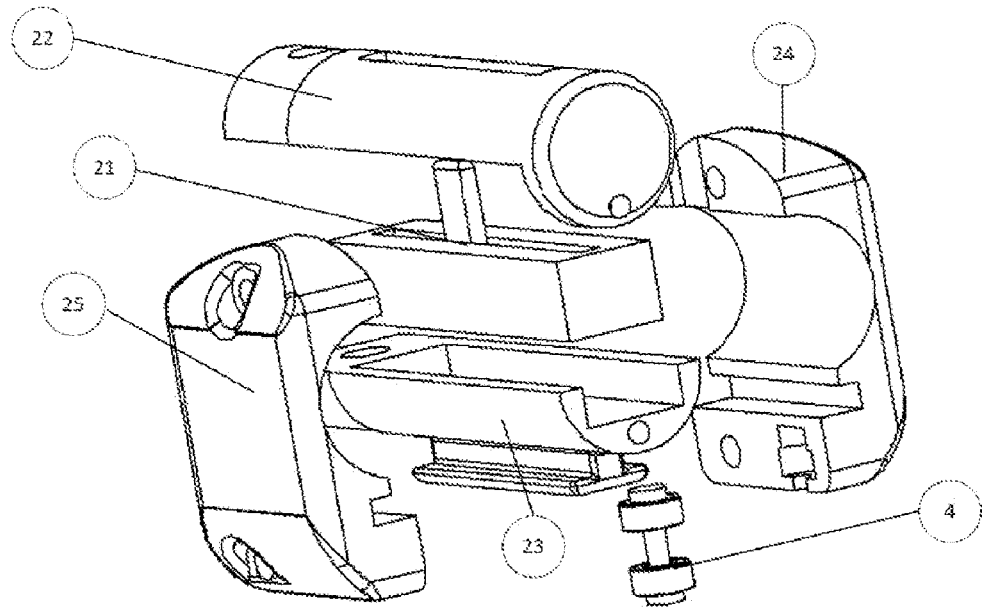
FIG. 3 represents the linear motion mechanism.
  No. (21) in FIG. 3 represents the linear potentiometer
  No. (22, 23) in FIG. 3 represents the place inside which the potentiometer is placed
  No. (24, 25) in FIG. 3 represents the cover of the mechanism to be sealed

FIG. 3 shows parts (3, 4) in FIGS. 1 and 2, represent a mechanism of transmission of linear motion, abduction, and adduction motion that helps in supporting the mechanical design. It consists of the following parts: linear potentiometer (21) to track the linear motion; part (22) where the potentiometer (21) is kept and has a linear motion path to allow the finger mechanism to slide through (21); part (23) is a designed part in which the potentiometer (21) is placed inside it, parts (24, 25) are slipped into it since it has a path to allow only linear motion; Parts (24, 25) represent the cover for parts (22, 23) and fix the potentiometer (21); part (4) in FIGS. 1 and 2 are placed in (24 and 25) to allow the finger to move to the right and left (adduction, abduction) and it consists of two ball bearings "682" and a metal column to stabilize them.

Figure 4:
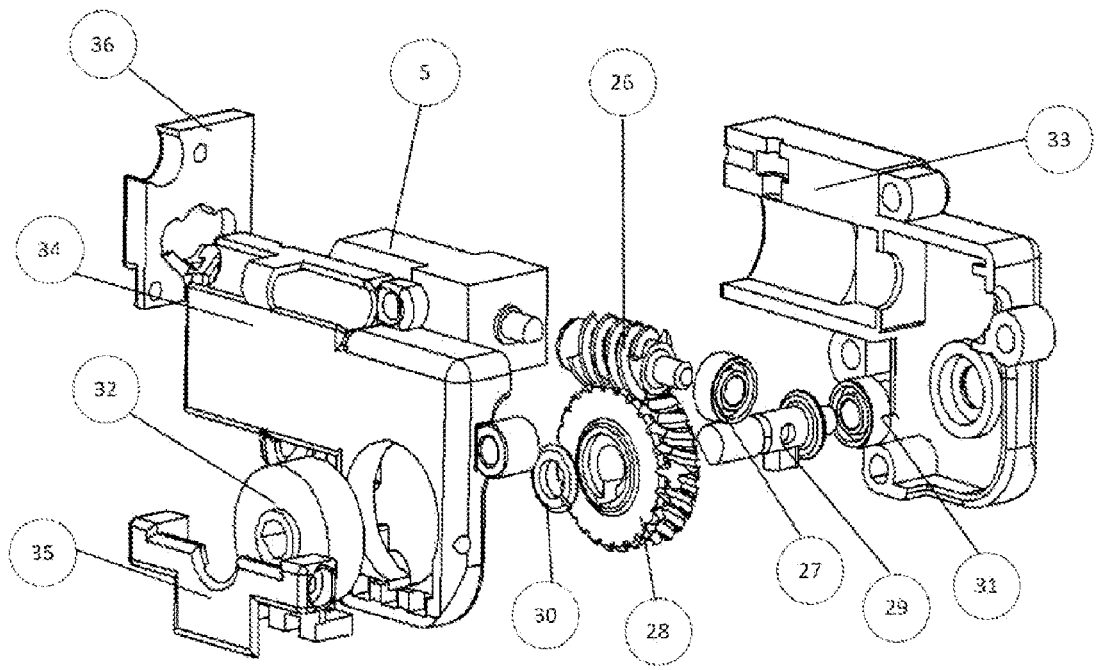
FIG. 4 represents the first gearbox
  No. (26) in FIG. 4 represents the worm with four beginnings
  No. (27, 31) in FIG. 4 represents a ball bearing single row 683
  No. (28) in FIG. 4 represents the 24 tooth worm gear
  No. (29) in FIG. 4 represents the shaft of the worm gear
  No. (30) in FIG. 4 represents a washer spring lock to fix the worm gear on the shaft
  No. (32) in FIG. 4 represents the angular potentiometer
  No. (34, 33) in FIG. 4 represents the body of the gearbox is tightly closed
  No. (36, 35) in FIG. 4 represents a cover to seal the mechanism

FIG. 4 shows part (6) in FIGS. 1 and 2, it is the gearbox that represents the mechanism for transmitting the rotational motion of the motor to an axis perpendicular to the motor axis at a lower speed and more torque. It also has a self-locking feature and helps in controlling the motor operation and the direction of rotation consists of the following parts: the worm (26) and worm gear mechanism (28) which is designed with a pitch of 2 mm and FIG. 4 shows part (6) in FIGS. 1 and 2 and it is the gearbox that represents the mechanism for transmitting the rotational motion of the motor to an axis perpendicular to the motor axis at a lower speed and more torque. It also has an self-locking feature and helps in controlling the motor operation and its direction of rotation, consists of the following parts: the worm (26) and worm gear mechanism (28) which is designed with a pitch of 2 mm and reduction ratio 6:1; an integrated shaft for the worm is fixed from the first end to the motor (5) and from the other end a ball bearing with a single-row ball "683" (27), that is installed in the shaft to carry the worm and prevent friction with the body of the gearbox (29); the shaft of the worm gear as it has a wide part on which the worm gear rests, a key to install the worm gear, a groove to put the split lock washer (30) to prevent the worm gear from the leaving the shaft and it also has a key to fix part (32) which is an angular potentiometer to carry the worm gear, prevents friction with the body of the gearbox and sends feedback information regarding the current position of the finger which helps in the process of operation and direction of rotation for the motors; a ball bearing with a single-row ball "683" (27), that is installed in the shaft to carry the worm gear and prevent friction with the body of the gearbox; the left cover of the gearbox (33), in which the ball bearing (31, 27), the DC motor (5) are attached to it, as well as the mechanism (4) to connect the mechanism (6) with (3); the right cover of the gearbox (34), in which the ball bearing (27), the angular potentiometer (32) which is covered by part (35), the DC motor (5) is attached to it, as well as the mechanism (4) to connect the mechanism (6) with (3), and it has paths for the passage of the wires of the next stage of the mechanisms and it is fixed through 4 screws (32). Part (36) closes them with 3 screws ratio 6:1; an integrated shaft for the worm is fixed from the first end to the motor (5) and from the other end a ball bearing with a single-row ball "683" (27), that is installed in the shaft to carry the worm and prevent friction with the body of the gearbox (29); the shaft of the worm gear which has a wide part on which the worm gear rests, a key to install the worm gear, a groove to put the split lock washer (30) to prevent the worm gear from the leaving the shaft and it also has a key to fix part (32) which is an angular potentiometer to carry the worm gear, prevents friction with the body of the gearbox, and sends feedback information regarding the current position of the finger which helps in the process of operation and direction of rotation for the motors; a ball bearing with a single-row ball "683" (27), that is installed in the shaft to carry the worm gear and prevent friction with the body of the gearbox; the left cover of the gearbox (33), in which the ball bearing (31, 27), the DC motor (5) are attached to it, as well as the mechanism (4) to connect the mechanism (6) with (3); the right cover of the gearbox (34), in which the ball bearing (27), the angular potentiometer (32) which is covered by part (35), the DC motor (5) is attached to it, as well as the mechanism (4) to connect the mechanism (6) with (3), and it has paths for the passage of the wires of the next stage of the mechanisms and it is fixed through 4 screws (32). Part (36) closes them with 3 screws.

Figure 5:
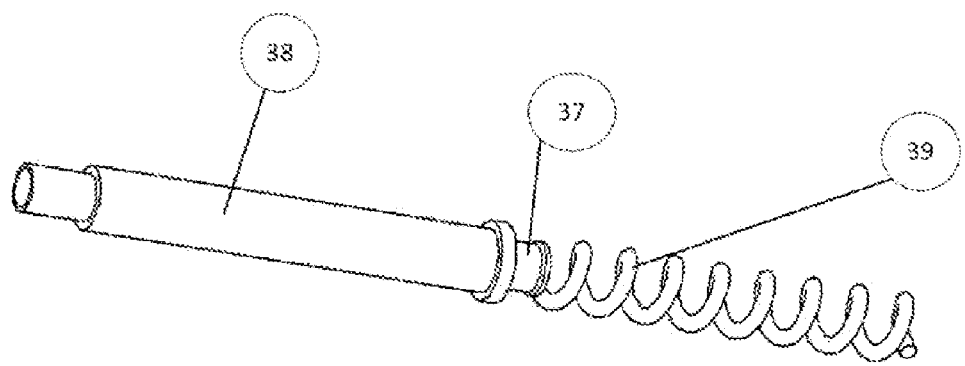
FIG. 5 represents the linear motion mechanism to allow rotation of the phalanges
  No. (37) in FIG. 5 represents the inner shaft that is fixed to the worm gear
  No. (38) in FIG. 5 represents the outer hollowed shaft allowing the inner shaft to slide into it
  No. (39) in FIG. 5 represents the spring inside the outer shaft

FIG. 5 is the mechanism (7) in FIG. 1 and it consists of a hollow shaft (38) to slide inside the shaft (37) and a spring (39) to always push it to expand, but they cannot separate from each other due to the nature of the dimensions of their diameter and composition.

Figure 6:
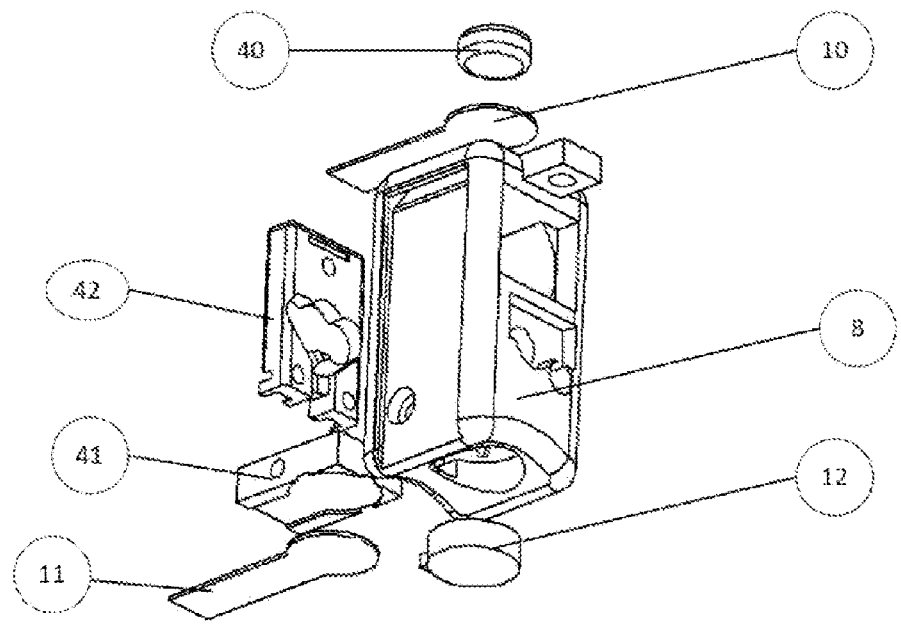
FIG. 6 represents the solid part that fix the proximal phalanges
  No. (40) in FIG. 6 represents the part that affects the force sensor in the flexion position
  No. (41) in FIG. 6 represents the part that lays under the extension force sensor
  No. (42) in FIG. 6 represents a cover to fix the upper force sensor

FIG. 6 displays parts (8, 10, 12, and 11) in FIG. 1, the design is fixed on the proximal phalanges and consists of part (41) have a cavity in which the force sensor (11) is placed and is fixed in part (8) through two screws; the vibration motor (12), which is placed below part (8) with space from part (11) to only affect the force sensor during the extension process for effective rehabilitation; the force sensor (10) is fixed on the surface of the part (8) and part (40) is placed over it to affect only the force sensor during the flexion process for effective rehabilitation; part (8) contains the motor (13) and the mechanism (7) and it has a duct for installing part (9) on its surface and a duct for the passage of the next mechanism wires; part (42) is fixed with part (8) through 3 screws and has a duct to fix the force sensor (10).

Figure 7:
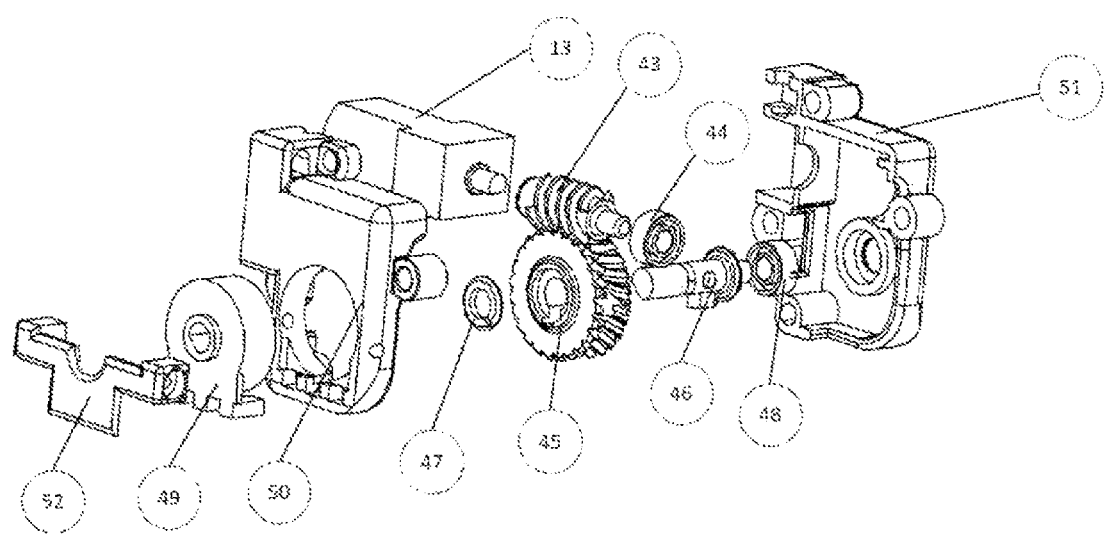
FIG. 7 represents the second gearbox
  No. (43) in FIG. 7 represents the worm with four beginnings
  No. (48, 44) in FIG. 7 represents a ball bearing single row 683
  No. (45) in FIG. 7 represents the 24 tooth worm gear
  No. (46) in FIG. 7 represents the shaft of the worm gear
  No. (47) in FIG. 7 represents a washer spring lock to fix the worm gear on the shaft
  No. (49) in FIG. 7 represents an angular potentiometer
  No. (51, 50) in FIG. 7 represents the body of the gearbox, which is sealed
  No. (52) in FIG. 7 represents a cover to seal the mechanism

FIG. 7 displays part (14) in FIGS. 1 and 2 and it is the gearbox that represents the mechanism for transmitting the rotary motion of the motor to an axis perpendicular to the motor axis at a lower speed and more torque. It also has a self-locking feature and helps in controlling the motor operation and its direction of rotation, it consists of the following parts: the worm (43) and worm gear mechanism (45) which is designed with a pitch of 2 mm and reduction ratio 6:1; an integrated shaft for the worm is fixed from the first end to the motor (13) and from the other end with (44), a ball bearing with a single-row ball "683" that is fixed in the shaft to carry the worm and prevent friction with the body of the gearbox; part (46) is the shaft of the worm gear as it has a wide part on which the worm gear rests, a key to install the worm gear, a groove to put the split lock washer (47) to prevent the worm gear from the leaving the shaft and it also has a key to fix angular potentiometer (49) to carry the worm gear, prevents friction with the body of the gearbox and sends feedback information regarding the current position of the finger, which helps in the process of operation and direction of rotation for the motors; a ball bearing with a single-row ball "683" (48), that is fixed in the shaft to carry the worm gear and prevent friction with the body of the gearbox; the left cover of the gearbox (51), in which the ball bearing (48, 44), the DC motor (13) is attached to it; the right cover of the gearbox (51), in which the ball bearing (44), the angular potentiometer (49) which is covered by part (52), the DC motor (13) are attached to it and it has paths for the passage of the wires of the next stage of the mechanisms and is fixed with (51) through 4 screws, and is fixed with part (8) through a screw and hole.

Figure 8:
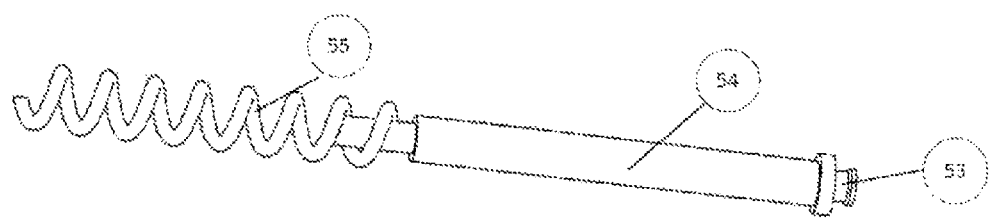
FIG. 8 represents the linear motion mechanism to allow rotation of the phalanges
  No. (53) in FIG. 8 represents the inner shaft that is fixed to the worm gear
  No. (54) in FIG. 8 represents the outer hollowed shaft allowing the inner shaft to slide into it
  No. (55) in FIG. 8 represents a spring outside the inner shaft

FIG. 8 is the mechanism (15) in FIG. 1. It consists of: a hollow shaft (54) in which the shaft (53) can be slipped; spring (55) is placed outside shaft (53) to always push it to expand, but it cannot be separated from shaft (54) due to the nature of their diameter and composition dimensions.

Figure 9:
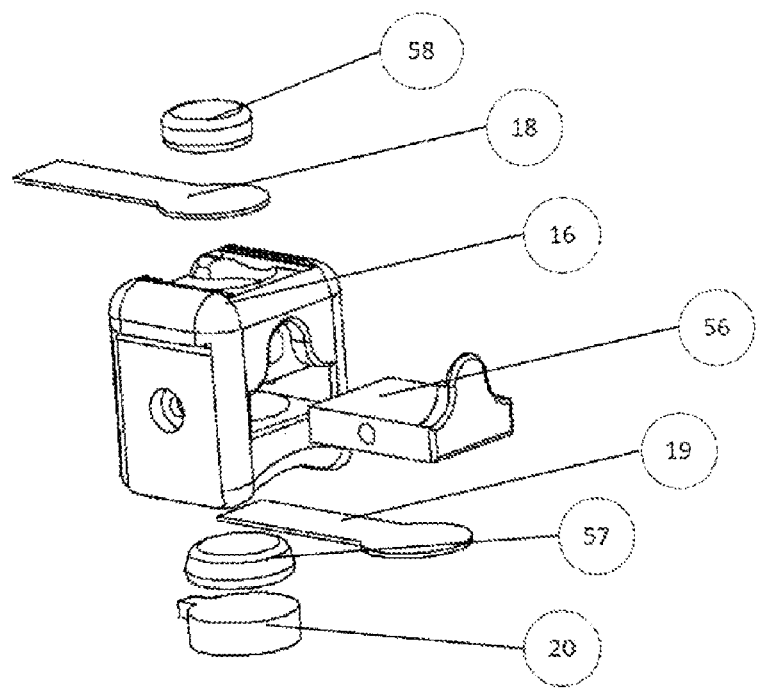
FIG. 9 represents the solid part that fix the middle or distal phalanges
  No. (58) in FIG. 9 represents the part that affects the force sensor in the flexion position
  No. (56) in FIG. 9 represents the part that lays under the extension force sensor
  No. (57) in FIG. 9 represents the part that affects the force sensor in the extension mode

FIG. 9 displays parts (16, 18, 19 and 20) in FIG. 1. The design is fixed on the middle or distal phalanges and consists of part (56) have a cavity in which the force sensor (19) is placed and is fixed in part (16) through two screws; the vibration motor (20), which is placed below part (16) with empty space from part (19) to only affect the force sensor during the extension process for effective rehabilitation, that through the transmission of the effect to part (57); the force sensor (18) is fixed on the surface of the part (16) and placed over part (58) to affect only the force sensor during the flexion process for effective rehabilitation; part (16) has the mechanism (15) fixed inside it, and it has a duct for installing part (17) on its surface.

Figure 10:
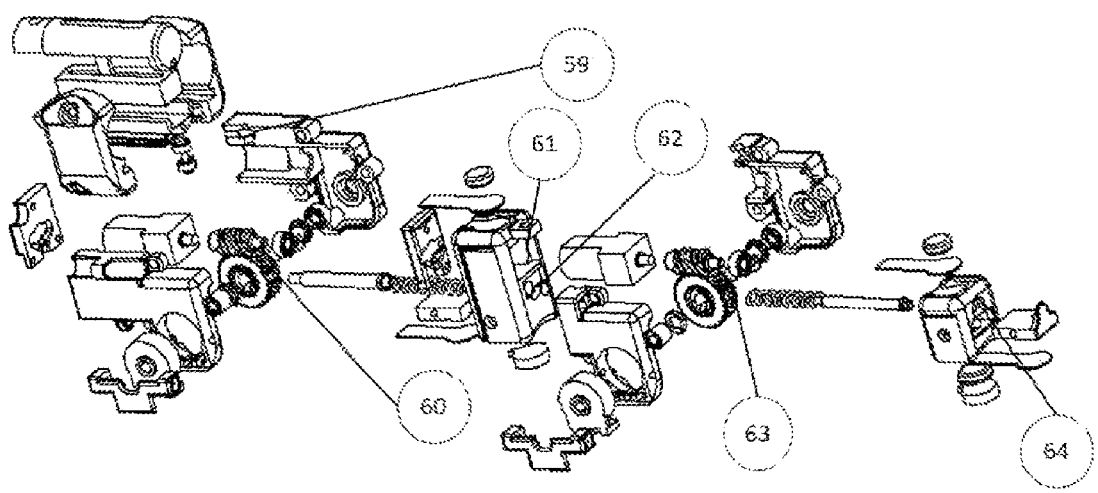
FIG. 10 represents the assembly of all the parts to form a finger of the device

FIG. 10 shows the method of assembling all the mechanisms to form one of the five fingers of the device. Part (59) shows the place of fixing mechanism (4) to connect mechanism (6) with (3). Part (60) shows the location of the installation of mechanism (7) inside the worm gear in the mechanism (6). Part (61) shows where the motor (13) is fixed with part (8). Part (62) shows the location of installation for the mechanism (7) with part (8). Part (63) shows the place of installation for mechanism (15) inside the worm gear in the mechanism (14). Part (64) shows the location of installation of mechanism (15) with part (16).

Figure 11:
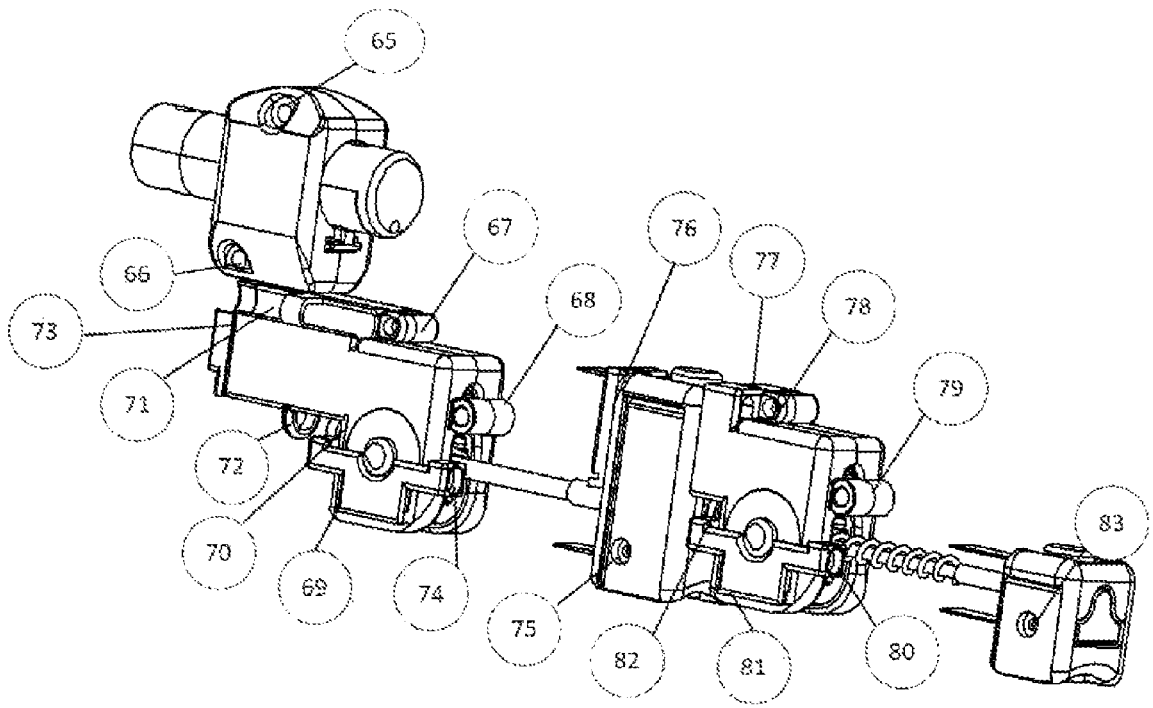
FIG. 11 represents the finger after assembly and shows the locations of the seals

FIG. 11 shows the installation of all parts to form one of the five fingers of the device. Parts (66, 65) are places for two screws to close the mechanism (3). Parts (67, 68, 69, 70) are places for four screws for good sealing of the mechanism (6). Parts (71, 72) are ducts through which the wires of other mechanisms pass. Part (73) is a cover for the first gearbox to cover the motor (5). Parts (74, 80) are holes for the mounting screw of the potentiometer's cover with the gearbox. Parts (75, 83) are holes for the mounting screw of the part on which the force sensors are placed (41, 56). Part (76) is the cover of the motor (13) and it controls the motion of the force sensor (10) and it is fixed with part (8) with three screws. Part (77) represents a screw that connects part (8) to the second gearbox. Parts (78, 79, 81, and 82) are screw holes for good sealing of the mechanism (14).

Figure 12:
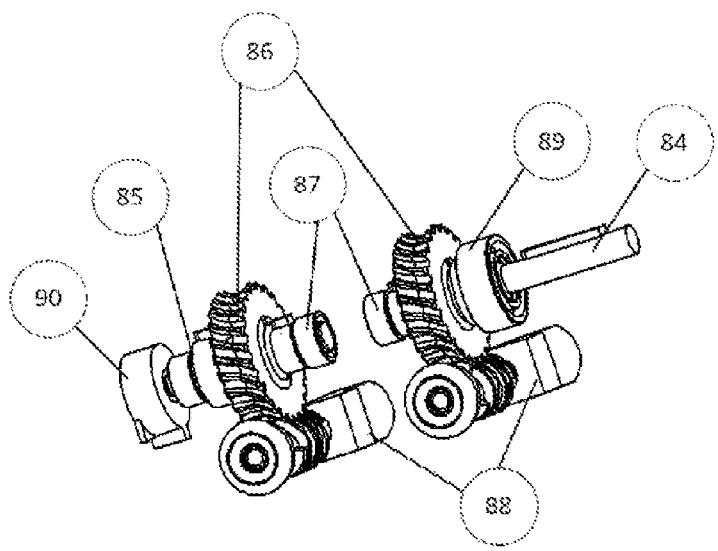
FIG. 12 represents the wrist rotation mechanism
  No. (84, 85) in FIG. 12 represents the shafts of the worm gear
  No. (86) in FIG. 12 represents the worm mechanism and the worm gear
  No. (87, 89) in FIG. 12 represents a ball bearing
  No. (88) in FIG. 12 represents DC motors
  No. (90) in FIG. 12 represents an angular potentiometer

FIG. 12 shows part (2) in FIG. 1, which is the mechanism for transmitting the rotational motion of the motor to an axis perpendicular to the axis of the motor with a lower speed and high torque to control the rotational motion of the wrist. It also has a self-locking feature and helps control the operation and rotation direction of the motor. It consists of the following parts: worm (88) and worm gear mechanism (86) designed with a pitch 3 mm, a reduction ratio 6:1 and an integrated shaft to the worm; parts (84, 85) are shafts that transmit the movement of the worm gear to the finger holder to move the wrist and it contains two ball bearing (87) and a potentiometer (90) are fixed on it, and it also has keys to install the worm gear and the finger holder; a ball bearing "605" (87) is installed in the shaft of the worm gear to carry the worm gear and prevent friction; an angular potentiometer (90) to hold the worm gear, prevents friction with the external structure and sends feedback information regarding the current position of the wrist, which helps in the process of operation and direction of rotation for the motors; there is a ball bearing and a ball bearing cover that fixes the worm in a straight line with the motor in the finger holder; micro DC geared motors with high torque (88), and they also represent part (1) in FIG. 1; ball bearing (89) to reduce friction and load the mechanism.

Figure 13:
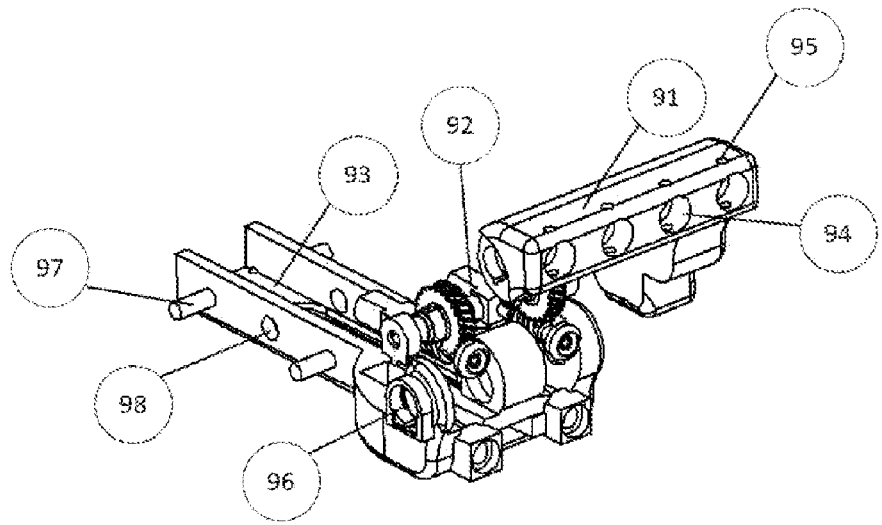
FIG. 13 represents the assembly of the finger holder, the forearm mold and the wrist movement mechanism
  No. (91) in FIG. 13 represents the finger holder
  No. (93) in FIG. 13 represents the forearm mold
  No. (92) in FIG. 13 represents the mechanism of wrist movement

FIG. 13 shows the method of assembling FIG. 12 with the finger holder and the forearm mold to control the rotational motion of the wrist. Comprises of the following parts: the finger holder (91) with a place (94) in which parts (22,23) in FIG. 3 are installed to hold the fingers at an angle of inclination of 30 degrees downward and 30 degrees opposite the thumb; hole (95) for a screw to install FIG. 3 with a finger holder; part (92) represents FIG. 12; forearm mold (93) that concentrates the device on the hand, it has holes designed for easy concentration and fixing of the parts of FIG. 12 inside it, it has ducts for the wires to pass from the motors and sensors to the control circuit and it connects with the finger holder through shafts (84, 85) in FIG. 12; the placing of the shaft of the mechanical wear and tear mechanism (98), consisting of a worm, a worm gear, a DC motor, and a shaft that is installed inside the worm gear and has screws on both sides in the opposite direction to transmit the motion of the motor to open and close the two sides of the forearm mold, through a push-button next to the box that is installed on the surface of the forearm mold to contain the electronic circuit; a shaft (97) for fixing the two sides of the forearm mold, lightening the load on the main shaft emerging from (98) and also for concentrating the device on the base specially designed for it to carry the device, lightening the load on the hand and allowing the rotational motion of "30 degrees" for the forearm; part (96) is the position of the potentiometer (90) in FIG. 12.

Figure 14:
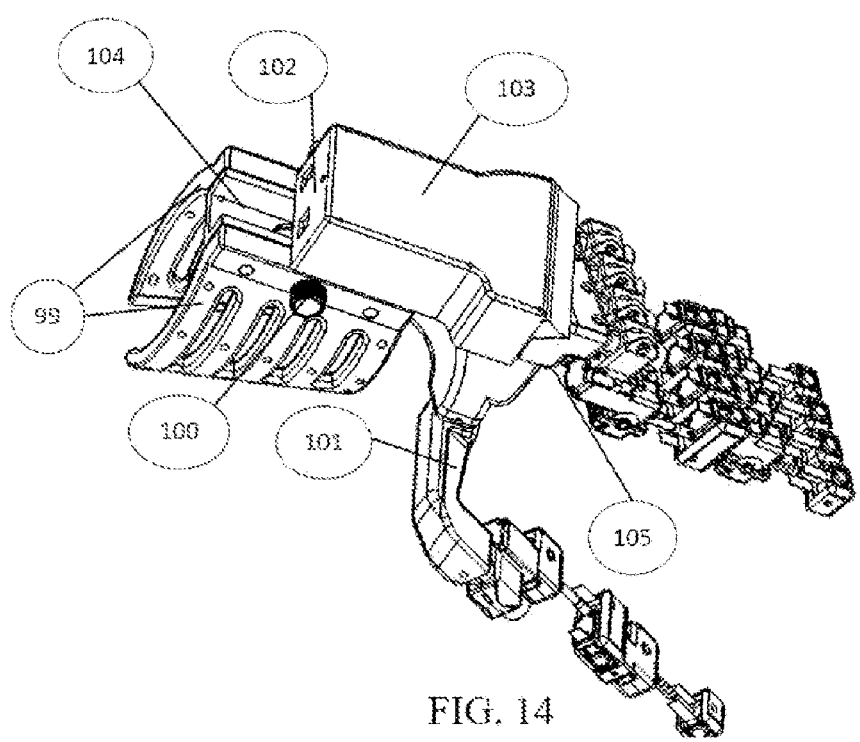
FIG. 14 represents the assembly of all parts of the device
  No. (99) in FIG. 14 represents two sides of the forearm mold
  No. (100) in FIG. 14 represents the mechanism of wearing the device automatically No. (101) in FIG. 14 represents the thumb holder No. (102) in FIG. 14 represents the electronic circuit box No. (103) in FIG. 14 represents the cover of the box

FIG. 14 shows all the mechanical parts of the device, which are: the right and left sides of the forearm mold (99) that concentrates the device on the hand and is designed in diameter and height to suit all hand sizes and also has a force sensor to control the automatic wearing of the device; thumb holder (101), fixed in the finger holder in the same way as before and holds the thumb mechanism with its own angle of inclination according to the nature of the movement of the thumb; the automatic wearing mechanism (100), which consists of a worm, a worm gear and a shaft with two opposite direction threaded ends to move away and bring together the two parts (99); the electronic circuit box of the device (102) that is fixed on the surface of the forearm mold and the electronic circuit is placed inside it; a cover (103) for part (102); a duct for wires (104) and (102) is fixed in it, and it contains the mechanism of part (100); a soft, non-stretchable belt (105) that holds the hand and on its surface at least one vibrator motor to relieve pain during use.

Figure 15:
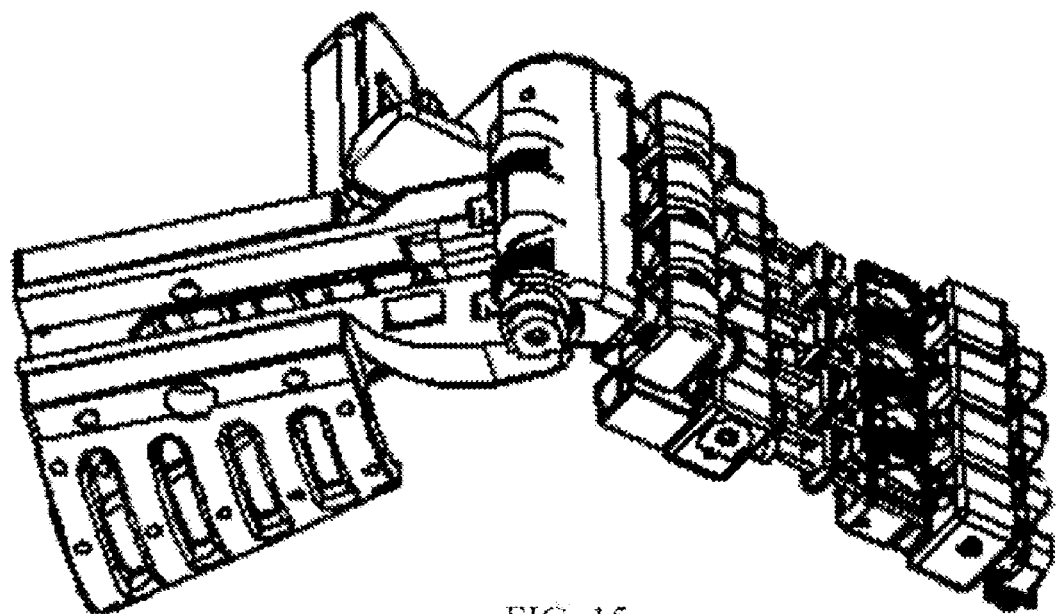
FIG. 15 represents all the mechanical parts of the device with an angle of inclination of "60 degrees" to the bottom of the wrist

FIG. 15 shows all the mechanical parts of the device with an angle of inclination of "60 degrees" to the bottom of the wrist.

Figure 16:
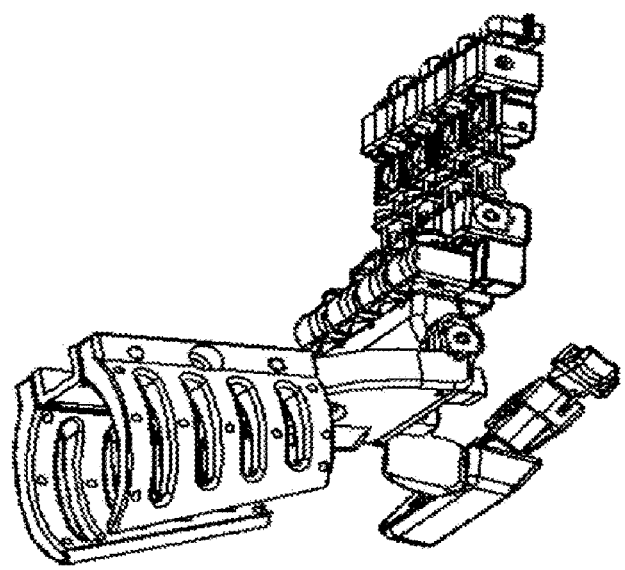
FIG. 16 represents all the mechanical parts of the device with an angle of inclination of "90 degrees" to the top of the wrist

FIG. 16 shows all the mechanical parts of the device with an angle of inclination of "90 degrees" to the top of the wrist.

Figure 17:
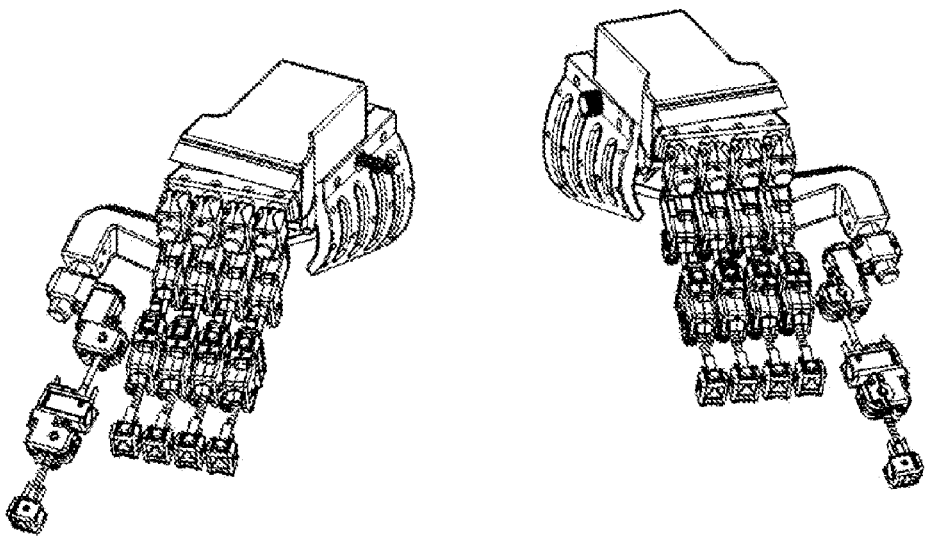
FIG. 17 represents the device for the right and left hand

FIG. 17 shows the device for the right and left hand.

Figure 18:
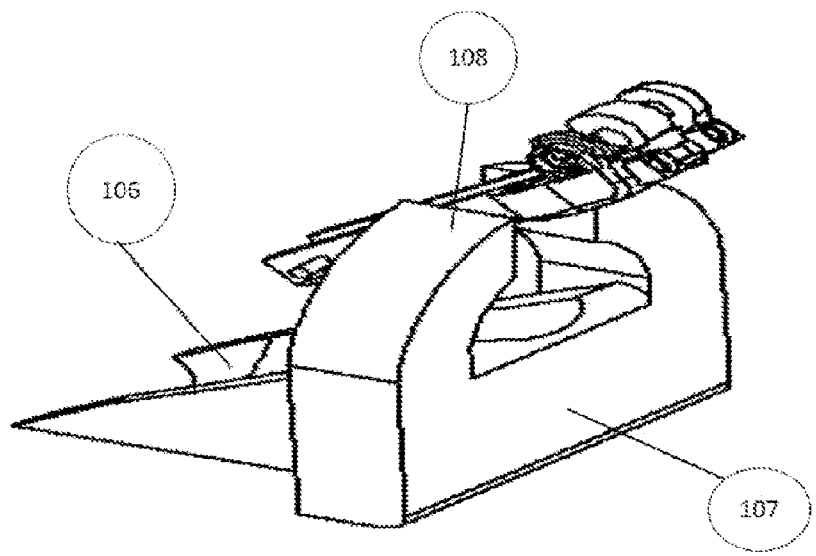
FIG. 18 represents the installation of the device on the base

FIG. 18 shows the fixation of the forearm mold with the base (107) is the base body and there are three wheels underneath for easy movement on the surface. A circular cavity (106) for the user to comfort his hand, designed in diameter and height to suit all hand sizes. A bore (108) where (97) in FIG. 13 passes through to carry the device, reduce the load on the hand and allow rotational movement of the forearm through the design of the groove.

Figure 19:
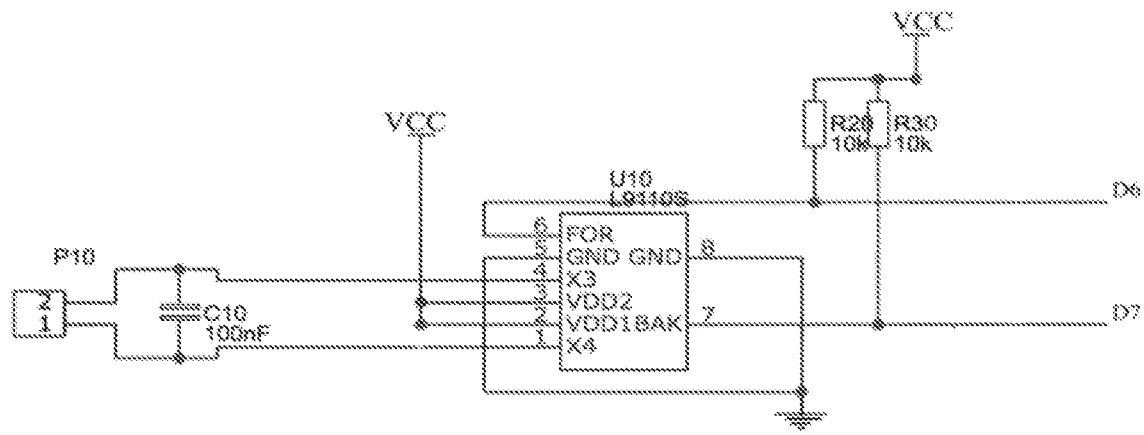
FIG. 19 represents the electronic circuit for controlling the speed and direction of rotation of the DC micro motor

FIG. 19 represents the electronic circuit (IC L9110) to control the speed and direction of rotation of the geared DC micro motor.

Figure 20:
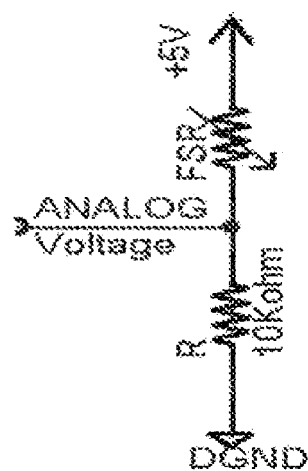
FIG. 20 represents the electronic circuit for receiving analog signals of the force sensor

FIG. 20 shows the electronic circuit for receiving the analog signals of the force sensor.

Figure 21:
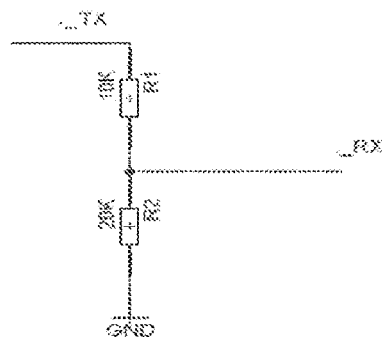
FIG. 21 represents the electronic circuit for connecting the microchip for wireless communication with the microcontroller

FIG. 21 shows the electronic circuit OF UART protocol. The (RX) of the wireless communication circuit is connected with the (TX) Microcontroller.

Figure 22:
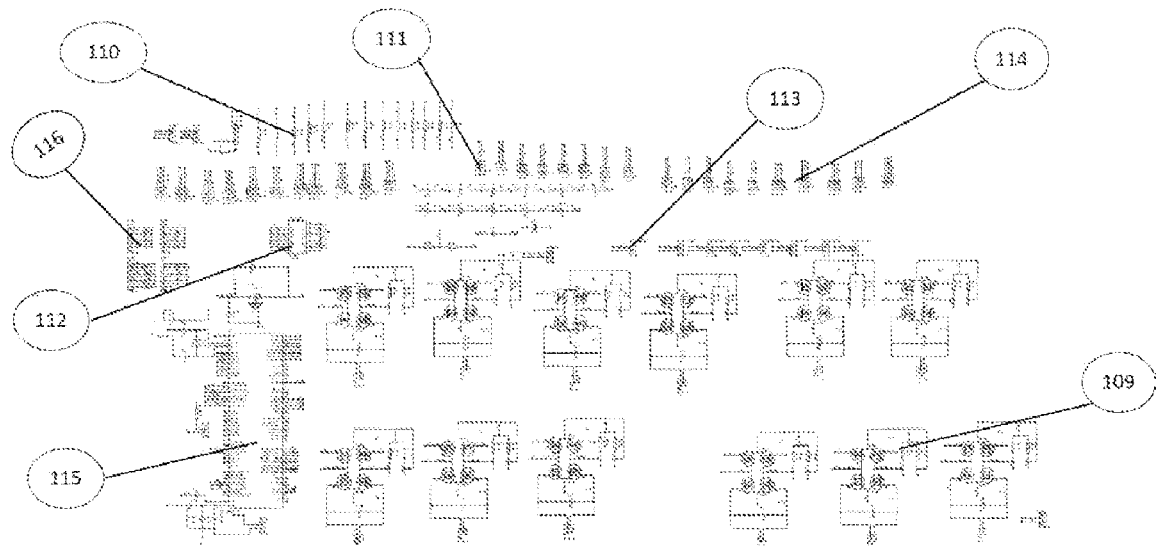
FIG. 22 represents the illustration of the electronic circuit of the device

FIG. 22 represents the illustration of the electronic circuit that contains: the microcontroller (115); motor driver circuits (109) like FIG. 19; receiver circuit (110), for the reading of force sensors, as shown in FIG. 20; wireless communication circuits (114, 115), such as FIG. 21.

Figure 23:
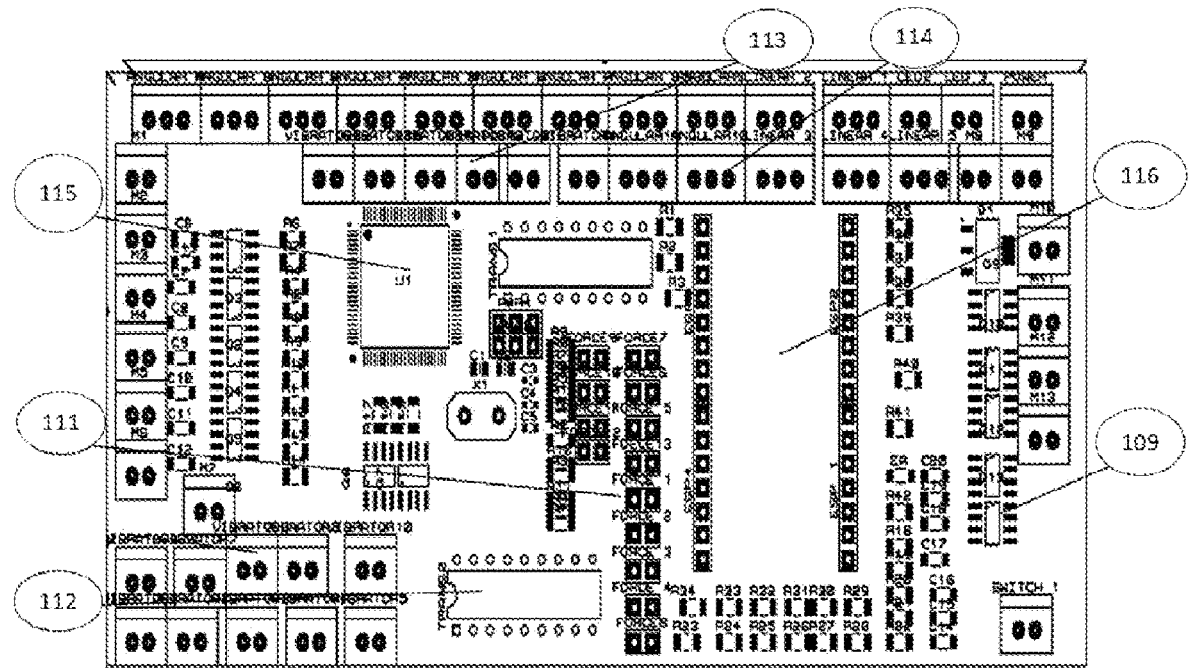
FIG. 23 represents the layout of the electronic circuit of the device
Figure 24:
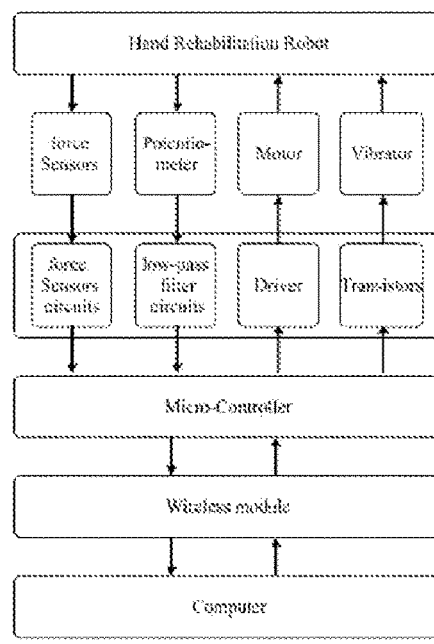
FIG. 24 represents the operations of the electronic system

FIG. 23 shows the electronic circuit layout, sensors connections input (111). Potentiometer connections input (114). Motor connections output (117). The transistors array (ULN 2803) (112) controls the operation of the vibration motors through the microcontroller (116). Microchip (116) for wireless communication. Power supply output for vibration motors (113). Microcontroller (115).

The device provides levels of differentiation for finger rehabilitation through independent motion control mechanisms for all ten phalanges of the fingers and the wrist with a full range of motion, which helps in focusing the work on each joint selectively. It relieves pain during exercises and stimulates the mechanoreceptors for all hand and wrist joints separately. The device is used in various injuries of the hand at different levels, whether it's a problem in the entire movement of the hand or a problem in a particular joint or a different level of injury to a different finger in the hand; the therapist can choose the joint and work on it with the level of training it needs, whether passive or active training, with a precise and easy to use system; the active and passive control of wrist movement with high accuracy; the active rehabilitation exercises reliance on a more stable and accurate source for measuring the force and making it the main element for controlling the level of training and movement, this is done through the electronic circuit (FIG. 23) that receives the reading of all the force and position sensors and gives orders to move following the position chosen by the patient for the session as it was programmed; It is also distinguished by working with the internet or without, and with a private account for each patient on the device's database to collect all the patient's data and represents it in statistics and graphs that directly displays the progress of his condition; through machine learning technology the user can obtain objective data for his condition and compare it with the optimum results for cases similar to motivate; the device needs only one energy source, which is electrical energy, so it is easy to move and can be used in various places, worn automatically, fits different hand sizes, and lightweight.

The Steps for Operating the Device are as Follows:

The mechanical design of the device works by providing the electrical power to the micro DC motor with its gearbox that reduces the speed and raises the torque from 1 to more than 300 and through the gearbox consisting of the worm and the worm gear that designed to transmit the movement in an axis perpendicular to the motor axis to reduce the speed and raise the torque six times to be able to fully control the movement of the patient's hand. An angular potentiometer is placed on the shaft of the worm gear to control the operation and the direction of rotation of the motor through sending feedback regarding the current position to the microcontroller continuously, that is to achieve the orders given to the microcontroller by the user, whether in the passive mode so gives an order at a certain angle or position or the active mode where is controlled by a force sensor located on the phalange of each motor. Three linear motion mechanisms are allowed to transfer the movement to fit different hand sizes. The first has a linear potentiometer that helps control and determine the user size of the device and the other two to transmit the movement of the worm gear to move the controlled phalanges accurately and easily. The user sets his program through the computer, which sends commands to the controller through Bluetooth or Wi-Fi. The controller receives the orders and processes them, then sends commands to the motors to work, receives the readings of the sensors, and after processing them, sends them to the computer to display and takes the decision regarding the operation and the direction of rotation of the motors. That is how the circuit of the device works while the operating steps are as follows:

Connect the power to the device

Connection with Bluetooth or the Internet

Turn on the computer

Adjusting the device size on the patient's hand to be suitable for wearing

Choose the appropriate mode to be used among the five modes.

When choosing the "passive" mode, two possibilities appear, the first is to enter the commands manually, and here a screen appears with a hand-drawn and a place on all the phalanges to enter the angle of inclination and the number of times in the order he wants, as he builds the program for the session and then presses start. The second is to choose the session number and here the program starts automatically to execute the saved code When choosing the "active" mode, he chooses from 3 active rehabilitation modes to represent the levels in order, either the active assisted, the free active, or the active resisted in its different degrees, and the session starts, and here a screen appears with real-time games, chooses his favorite and starts the session, as once he applies a simple force on the force sensors, within a relationship between the motors and a force sensor the motors start to work to help him in his movements according to the chosen position.

There is another screen that displays all the graphs and information about the patient's condition. From the beginning of using the device, the rehabilitation specialist can follow the progress of the patient's condition.

In the event of completion of the session or the desire to stop, he presses the stop button, the device moves to a resting position and then the motors stop working.

Most of the parts are made by injection molding with plastic material, 3D printing, and metalworking by (CNC). All components are installed in some way until the final product comes out with very high manufacturing accuracy.

What is claimed is:

1. An exoskeleton robot for the motor rehabilitation of a hand and wrist, comprising: at least two phalanx movement mechanisms configured to control the movement of each phalanx of a finger independently to form at least one mechanical finger configured to work on at least one joint selectively;

a mechanism configured to control the movement of the wrist;

at least two DC motors configured to generate rotational motion of the phalanges;

the at least two phalanx movement mechanisms comprising of at least two worm and worm gear mechanisms configured to transfer the rotational motion of the at least two DC motors to a general plane motion of the phalanx in an axis perpendicular to the motor axis and to make the at least two DC motors the sole controller of the motion with a self-locking feature;

at least one linear motion mechanism configured to adjust the device to the appropriate size for the patient to fit different hand sizes;

at least one adduction and abduction movement mechanism configured to allow rotational motion to the right and left for the at least one mechanical finger separately;

at least two force sensors configured on each phalanx of the finger to measure the force applied by the patient on the phalanx in the extension and flexion of the finger for an active-assisted rehabilitation and a resistant rehabilitation at their different levels for each joint separately;

a passive, an active-assisted and an active resistance rehabilitation mechanism configured for the wrist;

a plurality of vibration motors configured on all phalanges controlled to relieve pain on patients during training and stimulate mechanoreceptors for all joints of the hand and wrist;

the exoskeleton robot for the motor rehabilitation of the hand and wrist having at least four degrees of freedom of motion for the at least one mechanical finger, a degree of freedom for the wrist and a degree of freedom for the forearm when the device is configured to be placed on a forearm rest base;

a forearm mold configured to be placed on the patient's forearm in at least two different ways to carry the mechanism of the fingers and on the forearm mold surface an electronic circuit is installed;

a first method configured to place the forearm mold on the patient's forearm is through at least two parts on both sides of the forearm to place the forearm mold on the patient's forearm manually or automatically;

a second method configured to place the forearm mold on the patient's forearm is through the forearm rest base on which the forearm mold is attached;

a rechargeable battery for easy portability;

an electronic system including a computer to send the control command to the rehabilitation robot and to receive the sensor readings;

a wireless communication unit to connect the device to the computer;

a programmable microcontroller that controls the system by receiving the control command from the computer to complete the motion control and receiving sensor readings then sending them to the computer;

a driver unit to operate the at least two DC motors at different directions;

a transistor array to control the plurality of vibration motors;

the exoskeleton robots for the hand and wrist rehabilitation communicate with each other during a collective rehabilitation session of a group of patients.

2. The exoskeleton robot for the motor rehabilitation of the hand and wrist as in claim 1, wherein the four degrees of freedom of motion for the at least one mechanical finger, comprising: a first degree of freedom relates to a linear movement of the at least one mechanical finger in lengthening and shortening;

a second degree of freedom to a rotational movement that is configured to represent an abduction or adduction of the finger;

a third degree of freedom is a general plane motion configured to control a rotational movement of the proximal phalanges for the presence of the at least two phalanx movement mechanism at a higher level than the level of the proximal joint;

a fourth degree of freedom is a general plane motion configured to control a rotational movement of the middle or distal phalanges for the presence of the at least two phalanx movement mechanism at a higher level than the level of the middle or distal joint, which represents the movement of flexion and extension for a full range of motion for all fingers of the hand (0-90 degrees) independently for joints selectively.

3. The exoskeleton robot for the motor rehabilitation of the hand and wrist as in claim 1, wherein the general plane motion configured to control a rotational movement of the phalanges, comprising: the at least two DC motors to generate rotational movement;

the at least two phalanx movement mechanism to transmit the rotational motion of the motor for a general plane motion of a solid body configured to be placed on the phalanx in an axis perpendicular to the motor axis;

the solid body configured to be fixed on the phalanx and receiving the general plane motion from the at least two phalanx movement mechanism to move the phalanx up and down within the full range of motion;

an angular potentiometer installed directly on the at least two worm and worm gear mechanisms of the at least two phalanx movement mechanism configured to provide feedback regarding the current position of the phalanges continuously to control the movement of the phalanx.

4. The exoskeleton robot for the motor rehabilitation of the hand and wrist as in claim 3, wherein the at least two worm and a worm gear mechanisms comprise a solid shaft installed in the middle of the worm gear perpendicular to the axis of the worm gear to transmit the rotational motion of the worm gear;

a hollow shaft having a bore wherein the solid shaft slides into the hollow shaft and cannot be separated from each other due to their diameter's dimensions and composition that allow linear displacement;

a solid body configured to be placed on the phalanges having a bore where the hollow shaft fixed into to transmit the rotational movement of the worm gear to a general plane motion on the solid body configured to be placed on the surface of the phalanges for the rotational motion of the phalanx.

5. The exoskeleton robot for the motor rehabilitation of the hand and wrist as in claim 3, wherein the at least two worm and worm gear mechanism has a pitch of 2 mm and a reduction ratio of 6:1, further comprises: an integrated shaft to the worm having a bore where the DC motor shaft fixed into to save space;

a single-row ball bearing "683" is placed into the shaft to carry the worm and prevent friction with the body of the gearbox;

a worm gear shaft with a key to fix the worm gear;

a split lock washer is placed into a grove at the worm gear shaft to prevent the worm gear from leaving the shaft;

the angular potentiometer is placed into the key at the worm gear shaft to prevent the friction, save space and is configured to send information regarding the current position of the angle of inclination of the finger which helps the process of operating the motors and the direction of their rotation;

a single row ball bearing "683" is placed on the worm gear shaft from the other side to carry the worm gear and prevent friction with the body of the gearbox;

a body of the gearbox covers all the previous parts and has a plurality of paths for the passage of all wires.

6. The exoskeleton robot for the motor rehabilitation of the hand and wrist as in claim 1, wherein the at least one linear motion mechanism configured to adjust the device to the appropriate size for the patient, comprises: a linear potentiometer to track the linear motion;

at least two parts are installed inside the forearm mold where the linear potentiometer is placed inside them and they have a linear motion path to allow the finger mechanism to slide in a linear direction only and directly affect the output of the linear potentiometer;

at least two parts represent the cover for the previous two parts, and the first end of the at least one abduction and adduction motion mechanism is configured to be fixed with them for each finger separately.

7. The exoskeleton robot for the motor rehabilitation of the hand and wrist as in claim 1, wherein the at least one abduction and adduction motion mechanism is configured to allow right and left rotational motion for each finger individually, comprising: at least two ball bearings "682", one of them is fixed in the at least one linear motion mechanism and the other in a body of the phalanx motion mechanism to reduce friction during movement;

a metal shaft is placed into the ball bearings' bore to fix them and to be the axis of rotation of the finger to the right and left and to connect the at least one linear motion mechanism to the phalanx motion mechanism.

8. The exoskeleton robot for the motor rehabilitation of the hand and wrist as in claim 1, wherein the at least two force sensors are configured to be located on each phalanx of the finger to measure the force applied by the patient on the phalanx in the extension and flexion of the fingers for active-assisted and active resistance rehabilitation at their different levels for each joint individually;

a scaled knop to enter the threshold of appropriate resistance value for the patient's condition configured to be combined with the direction of force and the value of the force applied by the patient on all the phalanges through the microcontroller to be the resistance value, the direction of the force and the force value are the main controller of the movement of the motor;

a circular cavity above the surface of a solid body that is configured to be fixed on the phalanges, in which the at least two force sensors are configured to sense flexion force are placed;

a ring of the same size of the at least two force sensor is attached to a soft non-stretchable strap that is configured to connect the solid body to the phalanges to affect the at least two force sensors by flexing the fingers, so when the strap is configured to be stretched with the fingers in the flexion, the ring presses on the at least two force sensors and its reading changes;

a circular cavity under the solid body configured to be fixed on the phalanges to place the at least two force sensors configured to sense extension;

a ring is placed under the solid body to affect the at least two force sensors by extending the fingers, configured so when the patient presses with the patient's fingers on the ring in the direction of the extension, the motion is transmitted to the at least two force sensors changing their readings.

9. The exoskeleton robot for the motor rehabilitation of the hand and wrist as in claim 5, wherein the passive, active-assisted and active resistance rehabilitation mechanisms for the wrist, comprising: the at least two DC motors are further mounted on the same level above the forearm mold to generate kinetic energy;

the at least two worm and worm gear mechanisms further transmit the rotation motion of the at least two DC motors to an axis perpendicular to the motor axis configured to produce the rotational motion of the wrist with higher torque and less speed;

an integrated shaft for the worm loaded with a ball bearing to prevent friction and for alignment;

a ball bearing holds the shaft of the worm gear from both sides in the forearm mold to prevent friction and provide alignment;

the angular potentiometer is installed on the worm gear shaft to measure the angle of inclination of the worm gear from a straight angle;

the key in the worm gear shaft to fix the worm gear with a moving part that carries the finger mechanism;

a sensor to measure force and relate it to the speed of the motors motion and the direction of rotation;

a scaled knop to enter the threshold of appropriate resistance value for the patient's condition configured to be combined with the direction of force and the value of the force applied by the patient on all wrist through the microcontroller to be the resistance value, the direction of the force and the force value the main controller of the movement of the at least two DC motor;

the plurality of vibration motors, based on the wrist joint, are configured to relieve pain during training and stimulate the mechanoreceptors of the wrist joint;

wherein the entire motors and mechanisms are placed inside the forearm mold to reduce size.

10. The exoskeleton robot for the motor rehabilitation of the hand and wrist as in claim 1, wherein the plurality of vibration motors configured to be on all phalanges controlled to relieve pain on patients during training and stimulate mechanoreceptors for all joints of the hand and wrist, comprising: a micro-vibration motor is circular or coin-shaped, is placed under the solid body that is configured to be placed on each phalanx;

a micro-vibration motor is placed below a part that fixed the wrist joint;

a scaled knop to control the operation of each plurality of vibration motors separately or all plurality of vibration motors at the same time;

a scaled knop to choose the operating time of the plurality of vibration motors.

11. The exoskeleton robot for the motor rehabilitation of the hand and wrist as in claim 1, wherein the forearm mold is configured to be placed on the patient's forearm to carry a finger mechanism, comprising: a box where the electronic circuit is installed into and on the surface of the forearm mold;

a plurality of ducts for all the electrical wires;

at least two guide shafts embedded in the forearm mold serve as a path for the mechanism configured to move the two sides of the forearm with the forearm mold to allow entry of the patient's forearm into the robot or to fix the forearm mold on the base of the robot.

12. The exoskeleton robot for the motor rehabilitation of the hand and wrist as in claim 5, wherein the first method configured to fix the forearm mold to the patient's forearm, comprising: configuring at least two sides of the forearm to fix the forearm mold to the patient's forearm manually or automatically;

manually by using a screw with a knurling head and a nut to configurably connect the forearm mold and the two sides of the forearm together to control the size of entry for the patient's forearm by turning the screw manually;

automatically by using of the at least two DC motors that are placed in the middle of the forearm mold, the at least two worm and worm gear mechanism, the worm gear shaft with the key to fix the worm gear and a thread in two different directions for the two ends of the worm gear shaft to configurably connect the two sides of the forearm through an internal threading bore at the center of the worm gear, the at least two DC motor start by pushing a button configured to seal both sides of the forearm and the forearm mold automatically, a force sensor is configured to be placed on the surface of one of the two sides of the forearm to control stopping the movement of the at least two DC motor when the distance between the two sides of the forearm fits the size of the patient's forearm.

13. The exoskeleton robot for the motor rehabilitation of the hand and wrist as in claim 1, wherein the second method configured to fix the forearm mold to the patient's forearm, comprising: a forearm rest base on which the forearm mold is attached configured to reduce the load on the patient's hand;

a bore in which the forearm mold is fixed through the two guide shafts configured to allow rotational movement of the forearm;

at least three wheels at the bottom of the base for free motion of the device on the table and configured to facilitate the movement of a shoulder joint.

14. The exoskeleton robot for the motor rehabilitation of the hand and wrist as in claim 1, wherein the electronic system, comprising: recording training information such as movement and strength, and configured to provide a quantitative assessment to the patient and the rehabilitation therapist after the treatment represented in statistics and graphs that displays the results of the patient's progress with the computer;

the programmable microcontroller that acts as a system operator by receiving a control command from the computer to complete the control of the device's movement, receiving the readings of the sensors and sending sensors data to the computer at the same time;

the driver unit for receiving control commands for the at least two DC motors from the microcontroller and implementing the commands by operating the at least two DC motors in both directions at different speeds;

a transistor array to receive the control commands for the vibration motors from the microcontroller and implementing them by operating at least one vibration motor;

at least one low-pass filter circuit to receive the readings of the linear potentiometer and the angular potentiometer before sending them to the microcontroller;

at least two circuits for receiving the readings of the force sensors before sending them to the microcontroller.

\* \* \* \* \*